(12) United States Patent
Martin (10) Patent No.: US 11,311,646 B2
(45) Date of Patent: Apr. 26, 2022

(54) THERAPEUTIC MATERIAL (71) Applicant: ASTON UNIVERSITY, Birmingham (GB)

(72) Inventor: Richard Martin, Birmingham (GB)

(73) Assignee: ASTON UNIVERSITY, Birmingham (GB)

( * ) Notice: Subject to any disclaimer, the term of this patent is extended or adjusted under 35 U.S.C. 154(b) by 0 days.

(21) Appl. No.: 16/464,561

(22) PCT Filed: Nov. 29, 2017

(86) PCT No.: PCT/EP2017/080865
§ 371 (c)(1),
(2) Date: May 28, 2019

(87) PCT Pub. No.: WO2018/099997
PCT Pub. Date: Jun. 7, 2018

(65) Prior Publication Data
US 2020/0054784 A1 Feb. 20, 2020

(30) Foreign Application Priority Data
Nov. 30, 2016 (GB) .................................. 1620308

(51) Int. Cl.
*A61L 27/10* (2006.01)
*C03C 3/062* (2006.01)
*C03C 3/097* (2006.01)
*C03C 4/00* (2006.01)

(52) U.S. Cl.
CPC .............. *A61L 27/10* (2013.01); *C03C 3/062* (2013.01); *C03C 3/097* (2013.01); *C03C 4/0007* (2013.01); *A61L 2430/02* (2013.01)

(58) Field of Classification Search
None
See application file for complete search history.

(56) References Cited

FOREIGN PATENT DOCUMENTS

| WO | 2005/087274 A1 | 9/2005 |
|---|---|---|
| WO | 2016/027110 A1 | 2/2016 |
| WO | 2016/055650 A1 | 4/2016 |
| WO | 2016/172426 A1 | 10/2016 |

OTHER PUBLICATIONS

Chatzistavrou et al., "Sol-gel derived bioactive glass ceramics for dental applications", Non-Metallic Biomaterials for Tooth Repair and Replacement, 2013. (Year: 2013).*
Franchini et al.; "Gallium-containing phospho-silicate glasses: Synthesis and in vitro bioactivity;" Materials Science and Engineering C; 2012; pp. 1401-1406; vol. 32, No. 6.
Keenan et al.; "Relating ion release and pH to in vitro cell viability for gallium-inclusive bioactive glasses;" J Mater Sci; 2015; pp. 1107-1120; vol. 51, No. 2.
Keenan et al.; "Ga-Containing Bioactive Glass/Dextran-CMC Hydrogel Composites: Ion Release and Cell Viability;" 2015 41st Annual Northeast Biomedical Engineering Conference (NEBEC); 2015.
Zeimaran et al.; "Antibacterial properties of poly (octanediol citrate)/gallium-containing bioglass composite scaffolds;" J Mater Sci: Mater Med; 2015; pp. 1-11; vol. 27, No. 18.
Saravanapavan et al.; "Low-temperature synthesis, structure, and bioactivity of gel-derived glasses in the binary CaO—SiO2 system;" Journal of Biomedical Materials Research; 2000; pp. 608-618; vol. 54.
May 23, 2017 Search Report issued in British Patent Application No. GB1620308.5.
Feb. 28, 2018 Written Opinion of the International Searching Authority issued in International Patent Application No. PCT/EP2017/080865.
Feb. 28, 2018 Search Report issued in International Patent Application No. PCT/EP2017/080865.

* cited by examiner

*Primary Examiner* — Melissa L Fisher
(74) *Attorney, Agent, or Firm* — Oliff PLC (57) ABSTRACT

A bioactive glass composition for use in treating bone cancer includes 0.5-10 mol % gallium oxide or 1.0-20 mol % gallium nitrate/halide; 25 to 75 mol % silicon dioxide; 10 to 30 mol % calcium oxide and/or strontium oxide; up to 30 mol % sodium oxide; and up to 15 mol % phosphorous pentoxide. It may further comprise magnesium and/or potassium oxide. The bioactive glass composition may be positioned within a patient's bone post-surgery to promote apatite formation and to release gallium ions having a toxic effect on any remaining cancerous cells.

11 Claims, 6 Drawing Sheets

THERAPEUTIC MATERIAL

FIELD OF THE INVENTION

The present invention relates to a therapeutic material for use in treating bone cancer. In particular, this invention relates to a bioactive glass composition and methods of treating bone cancer using a bioactive glass composition.

BACKGROUND OF THE INVENTION

Survival for osteosarcoma patients is poor despite the aggressive use of surgery, chemotherapy, and/or radiotherapy. Therefore, to improve the clinical outcome, safe and effective therapeutic materials are required. The minimum key requirements for an effective therapeutic material for use in osteosarcoma therapy are (1) to successfully eradicate any residual tumour not excised during the surgery without being cytotoxic to the surrounding tissue and (2) to provide a suitable platform for the regeneration of new bone.

Bioactive glasses and bioactive glass-ceramics are a group of surface-reactive glass or glass-ceramic biomaterials which, when implanted into living tissue, induce formation of an interfacial bond between the biomaterial and the surrounding tissue. They are one of the most promising bone replacement/regeneration materials; they bond to existing bone, are degradable and can stimulate new bone growth by the action of their dissolution products on cells.

Commercially available 45S5 Bioglass® (a $SiO_2$—$CaO$—$Na_2O$—$P_2O_5$ based glass) exhibits class A bioactivity meaning it bonds to bone and stimulates new bone growth even away from the glass-bone interface. Bioglass® was originally developed to provide a controlled release of calcium and phosphorous ions under physiological conditions. The calcium and phosphorous ions precipitate into amorphous calcium phosphate which then crystallises into hydroxyapatite to form new bone mineral. Furthermore, gene expressions are upregulated through controlled release of calcium, phosphorus and silicon ions. Bioglass® has received FDA approval and has been in clinical use since 1985.

Whilst there has been considerable interest in developing and optimising bioactive glasses for bone regeneration little or no research has been undertaken on bioactive glasses specifically for bone cancer applications.

Whilst bioactive glasses have been developed for cancer therapy these glasses were developed for treating liver cancer and are not suitable for sarcoma applications. Instead these glasses were designed to provide a controlled dose of beta radiation via radioactive 90-Yttrium and 153-Samarium isotopes. Consequently the isotopes were contained in highly bio-inert alumina-silicate glasses. The incorporation of radioactive $^{90}Y$ or $^{153}Sm$ isotopes into these glasses means that the base glass must be highly insoluble to prevent the release of radioactive ions which could potentially circulate throughout the body once released. Given that bioactivity and regenerative powers of Bioglass™ stem from the controlled release of Ca, P and Si ions it is clear that the incorporation of radioactive beta emitting ions is clearly a non-viable approach.

Bioactive glasses have also been modified to incorporate metal ions for other medical applications. For example, cobalt ions have been added to bioactive glasses to enhance vascularisation and silver ions have been incorporated to enhance the antimicrobial properties of bioactive glasses.

Gallium (Ga) is the most widely used metal ion for cancer treatment with the exception of platinum. Based on its clinical efficacy, gallium nitrate (Ganite™) is used as a treatment for cancer-associated hypercalcaemia. Furthermore, gallium nitrate has been shown to inhibit increased bone turnover and to decrease osteolysis in patients with bone metastases from a variety of different cancers. Uptake of bioavailable gallium is however low when administered orally as a salt.

A site specific local delivery system for gallium would therefore be highly advantageous.

SUMMARY OF THE INVENTION

In a first aspect, the present invention provides a bioactive glass composition comprising gallium.

The bioactive glass composition provides a site specific delivery system for gallium. The composition can be provided in a patient's bones e.g. at a site where bone mass has been depleted after surgery to treat bone cancer e.g. osteosarcoma. The bioactive glass composition bonds to and stimulates new bone growth whilst the toxicity of the gallium destroys any residual cancerous cells not excised during the surgery (whilst not detrimentally affecting surrounding tissue).

Optional features of the invention will now be set out. These are applicable singly or in any combination with any aspect of the invention.

The term "glass composition" is used throughout this specification to encompass both bioactive glasses and bioactive glass-ceramics (which contain a crystalline phase in addition to the glass phase).

The term "bioactive" is used to means that the glass composition actively promotes apatite formation under physiological conditions (in situ/in vivo).

In preferred embodiments, the bioactive glass composition is a degradable bioactive glass composition i.e. it degrades/dissolves in physiological conditions to release gallium ions.

The chemical durability and dissolution of ions from a bioactive glass composition is strongly related to the network connectivity, and bioactive glasses have a typical network connectivity of ~2. If the connectivity exceeds ~3 the rate of dissolution of ions from the glass (in an aqueous medium such as simulated body fluid, SBF) reduces to the extent that bioactivity ceases.

The connectivity can be controlled by adjusting the ratio of network formers ($SiO_2$) to network modifiers (such as $Na_2O$, $P_2O_5$ and $CaO$). The network modifiers disrupt the Si—O—Si bonds in the bioactive glass composition to reduce the connectivity.

The inventors have found that the addition of gallium ions increases the network connectivity of the glass composition and therefore undesirably reduces the dissolution of the glass. Without wishing to be bound by theory, the inventors believe that gallium ions act primarily as a network former and enters the glass replacing Si primarily as a 4-fold tetrahedral although it is possible that some gallium enters the glass as a network intermediate i.e. acting as both a network former (4-fold) and network modifier (6-fold).

To counteract the reduction in solubility of the bioactive glass composition and retain a connectivity of around 2, the inventors found that it was necessary to modify the concentration of network formers e.g. silicon dioxide and/or network modifiers e.g. calcium oxide, sodium oxide or phosphorous pentoxide. For example, they found that reducing the concentration of $SiO_2$ in the bioactive glass composition compared to a glass composition without the gallium ions resulted in a soluble/degradable gallium-containing bioactive glass composition. The inventors found that 3 parts $SiO_2$ had to be omitted for every 1 part of gallium oxide added. A similar result may be obtained by increasing the amount of network modifiers (e.g. CaO, $P_2O_5$ or $Na_2O$) in the composition (which is effectively the same as reducing the relative silicon dioxide concentration).

The silicon dioxide may be present in an amount between 25 to 75 mol %, e.g. between 35 and 60 mol % such as between 35 and 52 mol % e.g. around 45 mol %.

The bioactive glass composition preferably comprises calcium oxide CaO and/or SrO. The calcium/strontium oxide may be present in an amount between 10 to 30 mol %.

The gallium is preferably provided as $Ga^{3+}$ ions in the form of a soluble oxide or salt such as gallium oxide $Ga_2O_3$, gallium nitrate $Ga(NO_3)_3$ (commercially available as Ganite™), or a gallium halide such as gallium fluoride $GaF_3$ or chloride $GaCl_3$.

In some embodiments, the composition contains greater than 0.5 mol % gallium oxide ($Ga_2O_3$) or greater than 1 mol % gallium nitrate/halide. The composition may contain up to 10 mol % gallium oxide or up to 20 mol % gallium halide/nitrate. In preferred embodiments, the composition contains between 1 and 5 mol % gallium oxide or between 2 and 10 mol % gallium nitrate/halide e.g. between 2 and 5 mol % gallium oxide or between 4 and 10 mol % gallium nitrate/halide such as around 3 mol % gallium oxide or around 6 mol % gallium nitrate/halide.

The bioactive glass composition may further comprise sodium oxide $Na_2O$. The sodium oxide may be present in an amount up to 30 mol % e.g. in an amount of 1-30 mol % such as between 6-30 mol %.

The bioactive composition may further comprise phosphorous pentoxide $P_2O_5$. The phosphorous pentoxide may be present in an amount up to 15 mol % e.g. in an amount of 1 to 15 mol % such as 1 to 10 mol %.

A preferred embodiment of the present invention provides a bioactive glass composition comprising:
  0.5-10 mol % gallium oxide or 1-20 mol % gallium nitrate/halide (and preferably 1-5 mol % gallium oxide or 2-10 mol % gallium nitrate/halide);
  25 to 75 mol % silicon dioxide (and preferably 35-55 mol % silicon dioxide);
  10 to 30 mol % calcium oxide and/or strontium oxide;
  up to 30 mol % sodium oxide (and preferably 1-30 mol % sodium oxide or 6-30 mol % sodium oxide); and
  up to 15 mol % phosphorous pentoxide (and preferably 1 to 15 mol % phosphorous pentoxide or 1 to 10 mol % phosphorous pentoxide).

Preferred embodiments contain silicon dioxide, calcium oxide and/or strontium oxide, sodium oxide, phosphorous pentoxide and gallium.

In these preferred embodiments, the silicon dioxide may be present in an amount between 25 to 75 mol %, e.g. between 35 and 55 mol %, the calcium oxide and/or strontium oxide may be present in an amount between 10 to 30 mol %, the sodium oxide may be present in an amount between 1 and 30 mol % e.g. between 6 and 30 mol % and the phosphorous pentoxide may be present in an amount between 1 and 15 mol % e.g. between 1 and 10 mol %.

Accordingly, this preferred embodiment may provide a glass composition comprising:
  0.5-10 mol % gallium oxide or 1-20 mol % gallium nitrate/halide (and preferably 1-5 mol % gallium oxide or 2-10 mol % gallium nitrate/halide);
  25 to 75 mol % silicon dioxide (and preferably 35-55 mol % silicon dioxide);
  10 to 30 mol % calcium oxide and/or strontium oxide;
  1 to 30 mol % sodium oxide (and preferably 6-30 mol % sodium oxide); and
  1 to 15 mol % phosphorous pentoxide (and preferably 1 to 10 mol % phosphorus pentoxide).

In an especially preferred embodiment, the bioactive glass composition comprises between 35.5 and 45.0 mol % $SiO_2$. For example, it may contain between 37.0 and 44.0 mol %, e.g. between 38.0 and 42.0 or between 39.0 and 40.0 mol % such as around 39.8 mol % $SiO_2$.

The bioactive glass composition may comprise greater than 26.9 mol % CaO. For example, it may comprise between 27.0 and 30.0 mol % e.g. between 27.5 and 29.5 mol % or between 28.0 and 29.0 mol % such as around 28.6 mol % CaO.

The bioactive glass composition may comprise greater than 24.4 mol % $Na_2O$. For example, it may comprise between 24.5 and 27.0 mol %, e.g. between 24.7 and 26.5 mol % or between 24.9 and 26.0 mol % such as around 25.9 mol % $Na_2O$.

The bioactive glass composition may comprise less than 3.1 mol % $P_2O_5$. For example, it may comprise between 2.7 and 3.0 mol % e.g. between 2.7 and 2.8 mol % $P_2O_5$.

Accordingly, this especially preferred embodiment may comprise:
  0.5-10 mol % gallium oxide or 1-20 mol % gallium nitrate/halide (and preferably 1-5 mol % gallium oxide or 2-10 mol % gallium nitrate/halide);
  35.5-45.0 mol % $SiO_2$ (and preferably 38.0-42.0 mol % e.g. around 39.8 mol %);
  27.0-30.0 mol % CaO (and preferably 28.0-29.0 mol % e.g. around 28.6 mol %);
  24.5-27.0 mol % $Na_2O$ (and preferably 24.9-26.0 mol % e.g. around 25.9 mol %); and
  2.7-2.8 mol % $P_2O_5$.

The bioactive glass composition comprising silicon dioxide and calcium oxide and/or strontium oxide, and optionally sodium oxide and/or phosphorous pentoxide composition may additionally comprise one or more of the following components:
  $K_2O$: from 0 to 15 mol %
  MgO: from 0 to 15 mol %
  ZnO: from 0 to 10 mol %
  $CaF_2$: from 0 to 15 mol %
  $CaCl_2$: from 0 to 15 mol %
  $B_2O_3$: from 0 to 10 mol %
  $Ag_2O$: from 0 to 10 mol %
  Other components: from 0 to 10 mol %

Another preferred embodiment of the present invention provides a bioactive glass composition comprising silicon dioxide, calcium oxide and/or strontium oxide, sodium oxide, phosphorous pentoxide, magnesium oxide and potassium oxide, the bioactive glass composition further comprising gallium.

In this preferred embodiment, the silicon dioxide may be present in an amount between 25 to 75 mol %, e.g. between 35 and 55 mol %, the calcium oxide and/or strontium oxide may be present in an amount between 10 to 30 mol %, the sodium oxide may be present in an amount between 1 and 30 mol % (e.g. between 6 and 10 mol %), the phosphorous pentoxide may be present in an amount between 1 and 15 mol % (e.g. between 1 and 10 mol %), the magnesium oxide may be present in an amount between 5 and 15 mol % (e.g. between 5 and 12 mol % such as around 10 mol %) and the potassium oxide may be present in an amount between 5 and 15 mol % (e.g. between 5 and 12 mol % such as around 10 mol %).

Accordingly, this preferred embodiment may provide a glass composition comprising:
- 0.5-10 mol % gallium oxide or 1 to 20 mol % gallium nitrate/halide (and preferably 1-5 mol % gallium oxide or 2-10 mol % gallium nitrate/halide);
- 25 to 75 mol % silicon dioxide (and preferably 35-55 mol % silicon dioxide); 10 to 30 mol % calcium oxide and/or strontium oxide;
- 1 to 30 mol % sodium oxide (and preferably 1-10 mol % or 6-10 mol % sodium oxide);
- 1 to 15 mol % phosphorous pentoxide (and preferably 1 to 10 mol % phosphorous pentoxide);
- 5 to 15 mol % magnesium oxide (and preferably between 5 and 12 mol % magnesium oxide); and
- 5 to 15 mol % potassium oxide (and preferably between 5 and 12 mol % potassium oxide).

In an especially preferred embodiment, the bioactive glass composition comprises between 40.0 and 53.0 mol % $SiO_2$. For example, it may contain between 45.0 mol % and 53.0 mol %, e.g. between 44.5 and 52.5 mol %, between 45.0 and 52.0 or between 47.0 and 50.0 mol % such as around 48.5 mol % $SiO_2$.

The bioactive glass composition may comprise less than 27.5 mol % CaO. For example, it may contain between 22.5 and 25.0 mol % e.g. between 23.0 and 24.5 mol % or between 23.5 and 24.0 mol % such as around 23.6 mol % CaO.

The bioactive glass composition may comprise less than 7.5 mol % $Na_2O$. For example, it may contain between 6.1 and 7.0 mol %, e.g. between 6.2 and 6.7 mol % or between 6.3 and 6.6 mol % such as around 6.4 or 6.5 mol % $Na_2O$.

The bioactive glass composition may comprise less than 2.1 mol % $P_2O_5$. For example, it may contain between 1.7 and 1.9 mol % e.g. around 1.8 mol % $P_2O_5$.

The bioactive glass composition may comprise between 7.9 and 9.0 mol % MgO, e.g. between 8.1 and 8.8 mol % or between 8.2 and 8.6 mol % such as around 8.3 or 8.4 mol % MgO.

The bioactive glass composition may comprise less than 9.5 mol % $K_2O$. For example, it may contain between 7.9 and 9.0 mol %, e.g. between 8.0 and 8.6 mol % or between 8.1 and 8.5 mol % such as around 8.3 or 8.4 mol % $K_2O$.

Accordingly, this especially preferred embodiment may comprise:
- 0.5-10 mol % gallium oxide or 1 to 20 mol % gallium nitrate/halide (and preferably 1-5 mol % gallium oxide or 2-10 mol % gallium nitrate/halide);
- 45.0-53.0 mol % $SiO_2$ (and preferably 47.0-50.0 mol % e.g. around 48.5 mol %);
- 22.5-25.0 mol % CaO (and preferably 23.0-24.5 mol % e.g. around 23.6 mol %);
- 6.1-7.0 mol % $Na_2O$ (and preferably 6.3-6.6 mol % e.g. around 6.4 mol %);
- 1.7-1.9 mol % $P_2O_5$ (and preferably around 1.8 mol %);
- 7.9-9.0 mol % MgO (and preferably 8.2-8.6 mol % e.g. around 8.4 mol %); and
- 7.9-9.0 mol % $K_2O$ (and preferably 8.1-8.5 mol % such as around 8.2 mol %).

The bioactive glass composition comprising silicon dioxide, calcium oxide and/or strontium oxide, sodium oxide, phosphorous pentoxide, magnesium oxide and potassium oxide may additionally comprise one or more of the following components:
- ZnO: from 0 to 10 mol %
- $CaF_2$: from 0 to 15 mol %
- $CaCl_2$: from 0 to 15 mol %
- $B_2O_3$: from 0 to 10 mol %
- $Ag_2O$: from 0 to 10 mol %
- Other components: from 0 to 10 mol %

In a second aspect, the present invention provides a bioactive glass composition comprising silicon dioxide, calcium oxide and/or strontium oxide, sodium oxide, phosphorous pentoxide, magnesium oxide, potassium oxide and optionally zinc oxide, the bioactive glass composition further comprising gallium.

In preferred embodiments, the silicon dioxide may be present in an amount between 25 to 75 mol %, e.g. between 35 and 55 mol %, the calcium oxide and/or strontium oxide may be present in an amount between 10 to 40 mol % (e.g. between 20 to 40 mol %), the sodium oxide may be present in an amount between 1 and 30 mol % (e.g. between 1 and 20 mol % or 1 and 10 mol %, such as between 1 and 5 mol %), the phosphorous pentoxide may be present in an amount between 1 and 15 mol % (e.g. between 1 and 10 mol %), the magnesium oxide may be present in an amount between 5 and 15 mol % (e.g. between 5 and 12 mol % such as around 8 mol %) and the potassium oxide may be present in an amount between 1 and 15 mol % (e.g. between 1 and 10 mol % or 1 and 5 mol % such as around 4 mol %). Zinc oxide may also be present in an amount up to 10 wt % e.g. between 1-10 wt % such as between 1 and 5 wt %.

Accordingly, this preferred embodiment may provide a glass composition comprising:
- 0.5-10 mol % gallium oxide or 1 to 20 mol % gallium nitrate/halide (and preferably 1-5 mol % gallium oxide or 2-10 mol % gallium nitrate/halide);
- 25 to 75 mol % silicon dioxide (and preferably 35-55 mol % silicon dioxide);
- 10 to 40 mol % calcium oxide and/or strontium oxide (and preferably 20 to 40 mol %);
- 1 to 30 mol % sodium oxide (e.g. between 1 to 20 mol % and preferably 1-10 mol % or 1-5 mol % sodium oxide);
- 1 to 15 mol % phosphorous pentoxide (and preferably 1 to 10 mol % phosphorous pentoxide);
- 5 to 15 mol % magnesium oxide (and preferably between 5 and 12 mol % magnesium oxide);
- 1 to 15 mol % potassium oxide (e.g. between 1 and 10 mol % and preferably between 1 and 5 mol % potassium oxide); and
- 0 to 10 mol % zinc oxide (e.g. between 1 to 10 mol % and preferably between 1 and 5 mol % zinc oxide).

In an especially preferred embodiment, the bioactive glass composition comprises between 40.0 and 53.0 mol % $SiO_2$. For example, it may contain between 40.0 mol % and 45.0 mol %, e.g. between 42.0 and 44.0 mol %, such as around 43.0 mol % $SiO_2$.

The bioactive glass composition may comprise less than 37.5 mol % CaO. For example, it may contain between 30.0 and 37.0 mol % e.g. between 32.0 and 36.0 mol % such as around 35.0 or 34.9 mol % CaO.

The bioactive glass composition may comprise less than 10.0 mol % $Na_2O$. For example, it may contain between 1.0 and 4.0 mol %, e.g. between 2.0 and 4.0 mol % such as around 3.5 mol % $Na_2O$.

The bioactive glass composition may comprise less than 3.0 mol % $P_2O_5$. For example, it may contain between 1.0 and 2.0 mol % e.g. around 1.1 mol % $P_2O_5$.

The bioactive glass composition may comprise between 6.0 and 9.0 mol % MgO, e.g. between 7.0 and 8.0 mol % such as around 7.7 or 7.8 mol % MgO.

The bioactive glass composition may comprise less than 7.0 mol % $K_2O$. For example, it may contain between 1.0 and 6.0 mol %, e.g. between 2.0 and 5.0 mol % or between 3.0 and 4.0 mol % such as around 3.5 mol % $K_2O$.

The bioactive glass composition may comprise less than 7.0 mol % ZnO. For example, it may contain between 1.0 and 6.0 mol %, e.g. between 2.0 and 5.0 mol % or between 3.0 and 4.0 mol % such as around 3.2 mol % ZnO.

Accordingly, this especially preferred embodiment may comprise:

- 0.5-10 mol % gallium oxide or 1 to 20 mol % gallium nitrate/halide (and preferably 1-5 mol % gallium oxide or 2-10 mol % gallium nitrate/halide);
- 40.0-53.0 mol % $SiO_2$ (and preferably 42.0-44.0 mol % e.g. around 43.0 mol %);
- 30.0-37.0 mol % CaO (and preferably 32.0-36.0 mol % e.g. around 35.0 mol %);
- 1.0-4.0 mol % $Na_2O$ (and preferably 2.0-4.0 mol % e.g. around 3.5 mol %);
- 1.0-2.0 mol % $P_2O_5$ (and preferably around 1.1 mol %);
- 6.0-9.0 mol % MgO (and preferably 7.0-8.0 mol % e.g. around 7.8 mol %);
- 2.0-5.0 mol % $K_2O$ (and preferably 3.0-4.0 mol % such as around 3.5 mol %); and
- 2.0-5.0 mol % ZnO (and preferably 3.0-4.0 mol % such as around 3.5 mol %).

The bioactive glass composition of the second aspect comprising silicon dioxide, calcium oxide and/or strontium oxide, sodium oxide, phosphorous pentoxide, magnesium oxide, potassium oxide and optionally zinc oxide may additionally comprise one or more of the following components:

- $CaF_2$: from 0 to 15 mol %
- $CaCl_2$: from 0 to 15 mol %
- $B_2O_3$: from 0 to 10 mol %
- $Ag_2O$: from 0 to 10 mol %
- Other components: from 0 to 10 mol %

In a third aspect, the present invention provides a bioactive glass composition according to the first aspect or second aspect as a medicament.

In a fourth aspect, the present invention provides a bioactive glass composition according to the first aspect or second aspect for use in the treatment of bone cancer e.g. osteosarcoma.

In a fifth aspect, the present invention provides a method of treating bone cancer e.g. osteosarcoma using a bioactive glass composition according to the first aspect or second aspect.

The method may comprise providing the bioactive glass composition within the patient at a site of depleted bone mass e.g. at a site where surgical bone removal has occurred.

The method may comprise forming a powder e.g. by grinding the bioactive glass composition and providing the bioactive glass composition as a powder within the patient.

In these methods, the bioactive glass composition will act to actively promote apatite formation under physiological conditions and the gallium ions will be toxic to any remaining cancer cells whilst having no undesirable effects on any other surrounding tissue.

BRIEF DESCRIPTION OF THE DRAWINGS

Embodiments of the invention will now be described by way of examples with reference to the accompanying drawings in which:

FIG. 9 shows (a) Phosphorus and (b) calcium XPS spectra of Ga-doped bioactive glass compositions following immersion in SBF for 7 days.

FIGS. 10 A-H show SEM images of Ga-doped bioactive glasses after immersion in SBF for 1 week. (A, C, E, G) 0, 1, 2, and 3% Ga glass surfaces at lower magnification (500×). (B, D, F, H) 0, 1, 2, and 3% Ga glass surfaces at higher magnification (3000×).

EXPERIMENTAL

Glass Preparation and Analysis

Melt-quench derived 45S5 Bioglass, $(SiO_2)_{46.1}(CaO)_{26.9}(Na_2O)_{24.4}(P_2O_5)_{2.6}$, and gallium doped analogues were prepared using $SiO_2$ (Alfa Aesar, 99.5%), $CaCO_3$ (Alfa Aesar, 99.95-100.5%) and $Na_2CO_3$ (Sigma-Aldrich, 99.5%), $NH_4H_2PO_4$ (Sigma-Aldrich, 99.5%), and $Ga_2O_3$ (Alfa Aesar, 99.99%).

The precursors were weighed in the appropriate molar ratio to give $(Ga_2O_3)_X(SiO_2)_{46.1-3X}(CaO)_{26.9}(Na_2O)_{24.4}(P_2O_5)_{2.6}$ where X=1, 2 and 3% as shown in Table 1 below. Figures in brackets show the resulting mass (in grams) of each component in the bioactive glass composition.

TABLE 1

|  | Control 45S5 Bioglass™ | Ex 1 Ga1% glass | Ex 2 Ga2% glass | Ex 3 Ga3% glass | Ex4 Ga4% glass | Ex5 Ga5% glass | Ex 6 Ga10% glass |
|---|---|---|---|---|---|---|---|
| $SiO_2$ | 46.1 | 43.9 (8.97) | 41.7 (8.33) | 39.8 (7.80) | 37.6 (7.24) | 35.5 (6.70) | 25.0 (4.30) |
| $Na_2O$ | 24.4 | 24.9 (5.25) | 25.4 (5.25) | 25.9 (5.25) | 26.4 (5.25) | 26.9 (5.25) | 29.4 (5.25) |
| CaO | 26.9 | 27.5 (5.23) | 28.1 (5.23) | 28.6 (5.23) | 29.1 (5.23) | 29.7 (5.23) | 32.4 (5.23) |

TABLE 1-continued

|  | Control 45S5 Bioglass™ | Ex 1 Ga1% glass | Ex 2 Ga2% glass | Ex 3 Ga3% glass | Ex4 Ga4% glass | Ex5 Ga5% glass | Ex 6 Ga10% glass |
|---|---|---|---|---|---|---|---|
| $P_2O_5$ | 2.6 | 2.7 (1.28) | 2.7 (1.28) | 2.8 (1.28) | 2.8 (1.28) | 2.9 (1.28) | 3.1 (1.28) |
| $Ga_2O_3$ | 0 | 1 (0.65) | 2.1 (1.30) | 3 (1.84) | 4 (2.40) | 5 (2.95) | 10 (5.38) |

Precursors were thoroughly mixed and placed into a 90% platinum-10% rhodium crucible. The crucible was placed into a furnace at room temperature and heated at a rate of 10° C./min to 1450° C. and held at this temperature for 90 min. The melt was then poured into a graphite mould which had been preheated to 370° C. and annealed at this temperature overnight before being allowed to cool slowly to room temperature.

Glass discs were cut using an IsoMet™ 1000 Precision Diamond Saw (Buehler). The discs, 10 mm diameter and 2 mm thick, were polished using a MetaServ® (Buehler) polishing machine to a finish of 0.06 µm using colloidal silica. Glass particles were prepared using a planetary ball mill (PM100, Retsch) and the particles were sieved to give a size distribution between 40 to 60 microns.

X-ray diffraction experiments were conducted using a Bruker D8 diffractometer operating at the copper $k_\alpha$ wavelength of 1.54 Å. The powdered glass samples were measured over a two theta range of 10 to 80° in 0.02° steps. Measurements were taken at one second per point and no smoothing was undertaken.

Figure 1:
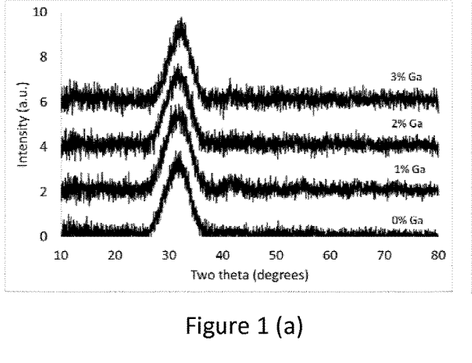
FIG. 1a shows the X-ray diffraction spectra of Ga-doped bioactive glass compositions.
FIG. 1b shows the X-ray diffraction spectra of Ga-doped bioactive glass compositions after exposure to SBF.

As shown in FIG. 1(a) the glasses of Example 1-3 were completely amorphous with no visible signs of Bragg peaks when examined using X-ray diffraction.

Further Ga-doped bioactive glasses were prepared using $SiO_2$, $CaCO_3$, $Na_2CO_3$, $NH_4H_2PO_4$, $MgCO_3$, $K_2CO_3$ and $Ga_2O_3$ (and ZnO for Example 13) along with an un-doped control having the formula $(SiO_2)_{54.6}(CaO)_{22.1}(Na_2O)_6$ $(P_2O_5)_{1.7}(MgO)_{7.7}(K_2O)_{7.9}$ as shown in Table 2 below.

TABLE 2

|  | Control 13-93 glass | Ex 7 Ga1% glass | Ex8 Ga2% glass | Ex 9 Ga3% glass | Ex 10 Ga4% glass | Ex 11 Ga5% glass | Ex 12 Ga10% glass | Ex 13 Ga3% glass |
|---|---|---|---|---|---|---|---|---|
| $SiO_2$ | 54.6 | 52.5 | 50.5 | 48.5 | 46.4 | 44.4 | 34.1 | 43.0 |
| $Na_2O$ | 6.0 | 6.1 | 6.3 | 6.4 | 6.6 | 6.7 | 7.4 | 3.5 |
| CaO | 22.1 | 22.6 | 23.1 | 23.6 | 24.1 | 24.6 | 27.2 | 34.9 |
| $P_2O_5$ | 1.7 | 1.7 | 1.8 | 1.8 | 1.9 | 1.9 | 2.1 | 1.1 |
| MgO | 7.7 | 8.1 | 8.3 | 8.4 | 8.6 | 8.8 | 9.7 | 7.8 |
| $K_2O$ | 7.9 | 7.9 | 8.1 | 8.2 | 8.4 | 8.6 | 9.5 | 3.5 |
| $Ga_2O_3$ | 0 | 1 | 2 | 3 | 4 | 5 | 10 | 3 |
| ZnO | 0 | 0 | 0 | 0 | 0 | 0 | 0 | 3.2 |

Precursors were thoroughly mixed and placed into a 90% platinum-10% rhodium crucible. The crucible was placed into a furnace at room temperature and heated at a rate of 10° C./min to 1450° C. and held at this temperature for 90 min. The melt was then poured into a graphite mould which had been preheated to 370° C. and annealed at this temperature overnight before being allowed to cool slowly to room temperature.

Glass discs were cut using an IsoMet™ 1000 Precision Diamond Saw (Buehler). The discs, 10 mm diameter and 2 mm thick, were polished using a MetaServ® (Buehler) polishing machine to a finish of 0.06 µm using colloidal silica. Glass particles were prepared using a planetary ball mill (PM100, Retsch) and the particles were sieved to give a size distribution between 40 to 60 microns.

Apatite Formation

A simulated body fluid (SBF) solution was prepared using the method outlined by Saravanapavan and Hench in *Journal of Biomedical Materials Research* 54, 608-618. SBF emulates the salt ion concentrations found in human blood plasma and can be used to test for the formation of hydroxyapatite in vitro.

The three gallium containing glasses of Examples 1-3 containing 1%, 2% and 3% together with the control glass (45S5) were placed in separate containers and 40 ml of SBF salt ion solution was added. The samples were sealed and maintained at 37° C. for 7 days. After reacting in SBF the samples were removed and rinsed with distilled water and acetone to remove any residual salts and halt reactions. Samples were dried at 60° C. and then assessed for apatite formation using X-ray diffraction.

A visible layer of hydroxyapatite was observed to have formed on the glass surface. X-ray diffraction confirmed the surface layer was an amorphous calcium phosphate/poorly defined hydroxyapatite (FIG. 1b) which is consistent with results typically observed for bioactive glasses. No reduction in apatite formation was observed for the gallium containing glasses compared to the 45S5 control.

Fourier Transform Infrared Spectroscopy. (FT-IR) spectra were recorded using a Thermo Nicolet IS50 infrared spectrometer fitted with a single bounce diamond ATR crystal. Spectra were recorded from 400 to 4000 cm-1 with a step size of 0.05 cm-1. All measurements were undertaken at room temperature and a total of 64 scans were recorded per sample.

Figure 8:
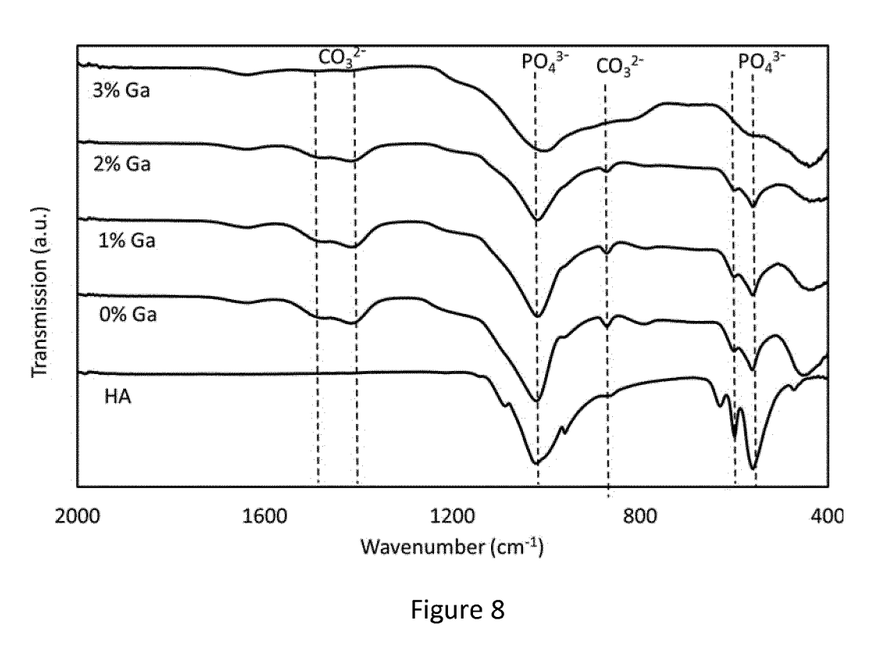
FIG. 8 shows FT-IR spectra of Ga-doped bioactive glass compositions following immersion in SBF for 7 days.

FTIR spectra for the gallium doped bioglasses, after immersion in SBF for 1 week, are shown in FIG. 8 together with a spectra of pure hydroxyapatite for reference. Each of the spectra exhibit the characteristic hydroxyapatite bands at 560, 600, and 1018 $cm^{-1}$.

X-ray Photoelectron Spectroscopy. (XPS) measurements were performed using a Kratos axis HSi XP spectrometer fitted with a charge neutralizer and Mg kα anode (1253.6 eV) and a base pressure of 5×10-9 Torr. Samples were loaded via adhesion onto carbon tape and spectra were calibrated to adventitious carbon (284.8 eV). Spectra were fit using CASA v2.3.15 using Gaussian-Lorentz (30) peak shapes and background subtracted with a Shirley background. Calcium peaks were fit with a doublet separation of 3.5 eV and phosphorus peaks with a doublet separation of 0.87 eV.

(SEM) images were recorded using a Carl Zeiss EVO MA10 scanning electron microscope operating at 10 kV and a working distance of 12.5 mm. The bioactive glass discs were immersed in SBF and maintained at 37° C. for 1 week. The samples were then removed, rinsed with water and acetone to remove residual salts and halt any further reactions. The samples were mounted onto SEM stubs using conductive carbon tape and splutter coated with gold. Images were recorded at magnifications of 500× and 3000×.

Figure 9A:
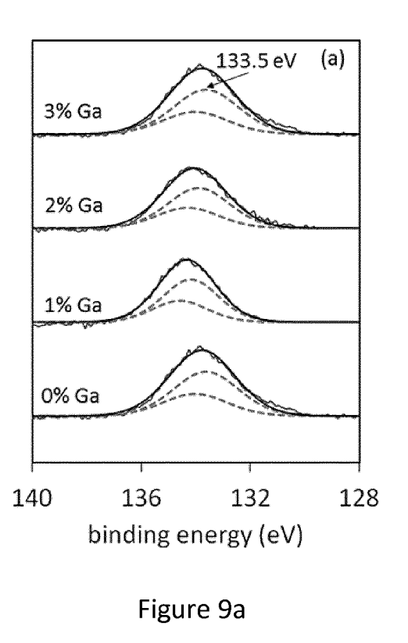
Figure 9B:
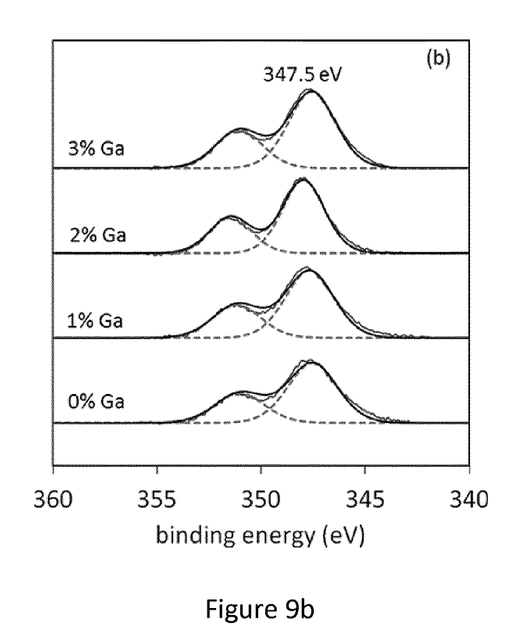
Figure 10:
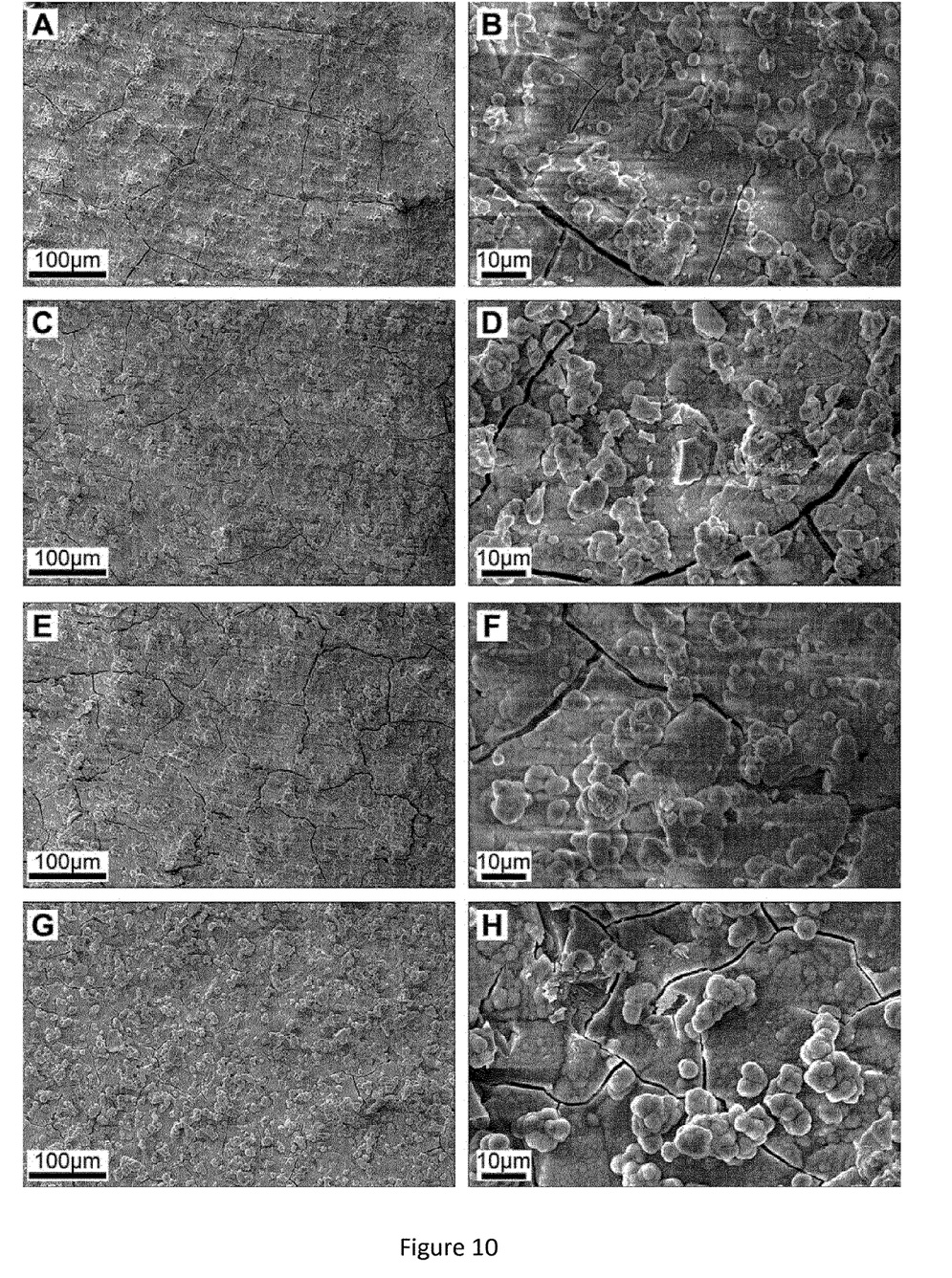

FIGS. 9a and 9b show XPS analysis of the glass surface following submersion in simulated body fluid for 1 week. This analysis revealed Ca:P ratios consistent with hydroxyapatite (Ca:P atomic ratio≈1.64±0.02) for all samples, corroborating the findings from X-ray diffraction. The Ca 2p3/2 peak binding energy was found to be ~347.5 eV and phosphorus 2p3/2~133.5 eV, again consistent with previously reported literature values for Ca2+ and P5+ within an apatite formation.

Figure 4:
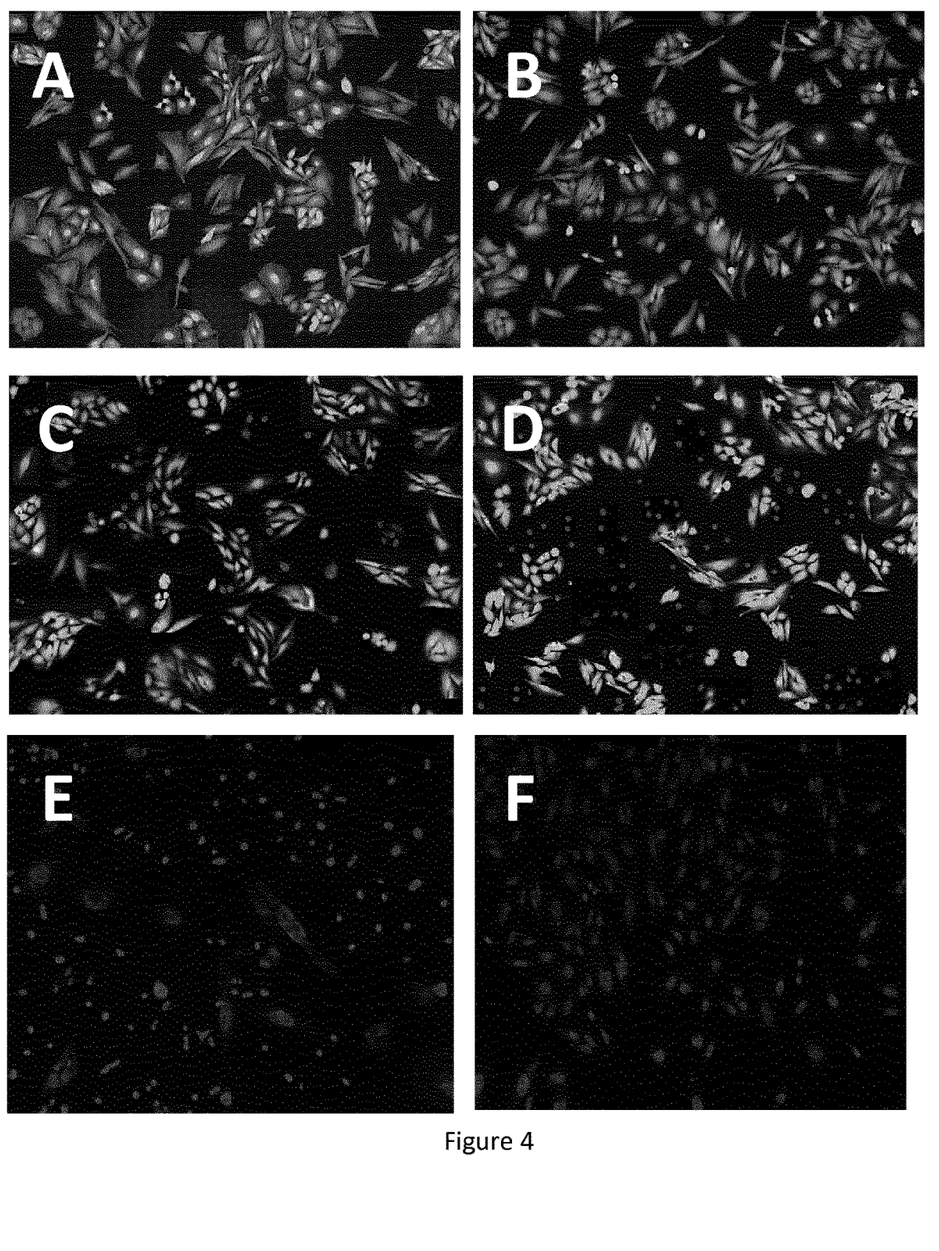
FIGS. 4A-4F shows fluorescence images of live/dead staining of Saos-2 cells cultured for 72 hours in conditioned media containing Ga-doped bioactive glass compositions.

FIG. 4 shows the glass surface following immersion in SBF for 1 week. As shown there is full surface coverage after 1 week. All samples show similar features; a relatively smooth surface layer composed of smaller fused spherical apatite precipitates is clearly visible. Termination of the surface reaction using acetone caused dehydration and cracking of the apatite layer. Larger fused apatite spheres, as typically observed for bioglass are seen on top of this initial layer.

ICP Analysis of Dissolution Products

To determine the concentration of ions released from the bioactive glasses, ICP analysis was conducted.

Stock solutions of 10 mg/ml of ground bioactive glass (Examples 1-3) in ultra-pure water were prepared for quantitative ionic profile using inductively coupled plasma optical emission spectrometry ICP-OES (iCAP™ 7000 Plus Series). Solutions were maintained at 37° C. for up to 3 days. Reference standards were used to calibrate the concentrations and the amount of each ion was calculated from the linear portion of the generated standard curve.

Figure 2:
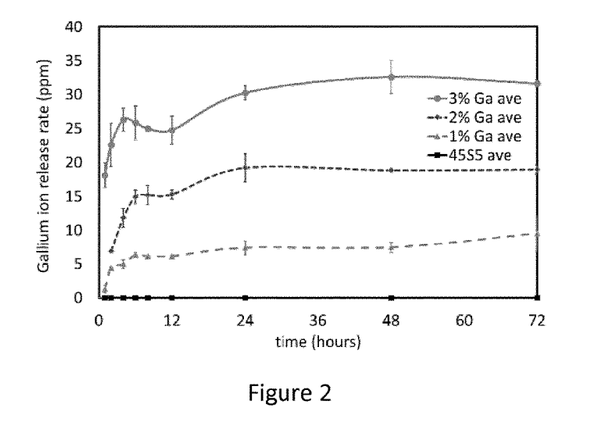
FIG. 2 shows release of gallium ions from Ga-doped bioactive glass compositions.

The concentration of gallium ions released in distilled water as a function of time for 10 mg/ml solutions are given in FIG. 2. A rapid release of ions was observed during the first few hours followed by a slower more gradual increase in ion concentration. As expected the concentration of gallium ions increases in an approximately linear trend with increasing gallium oxide content. At 24 hours the average gallium ion concentrations were 7.3, 18.8 and 30.2 ppm for the Ga 1%, Ga 2% and Ga 3% respectively. The gallium concentration approximately stabilised after 24 hours and minimal increases in concentrations were observed at 48 and 72 hours.

The release rate of Ca, P and Si is essential for upregulating gene expression. The ion concentrations are not significant for altered Ca, P and Si due to the incorporation of gallium oxide into the glasses. For example, at 24 hours the concentration of Si is 65, 70, 61 and 67 ppm for 45S5 (control), Ga 1% (Example 1), Ga 2% (Example 2) and Ga 3% (Example 3) respectively.

Cell Toxicity

Human osteosarcoma (Saos-2) cells were purchased from the American Tissue Culture Collection and maintained in McCoy's 5A medium containing 1.5 mM L-glutamine and 2200 mg/L sodium bicarbonate. Media was supplemented with 1% penicillin, streptomycin and 15% foetal bovine serum (FBS).

Human osteoblasts (NHOst) were purchased from Lonza and cultured in Clonetics OGM Osteoblast growth media supplemented with 10% FBS, 1% L-glutamine and 1% penicillin, streptomycin. Both cell lines were maintained at 37° C. in a humidified atmosphere of 5% $CO_2$/95% air.

Stock solutions of conditioned media were prepared by dissolving glass particles (from Example 1-3) in complete McCoy's 5A medium to treat Saos-2 cells and Clonetics OGM Osteoblast complete growth media to treat osteoblasts.

Stock solutions were prepared at a concentration of 10 mg/ml and left to incubate in a shaker incubator at 250 rpm at 37° C. for 24 hours. Following the 24 hour incubation period, stock solutions were filtered using 0.2 micron syringe filter. 3 ml samples were excluded to record stock solution pH values following glass dissolution.

Figure 3:
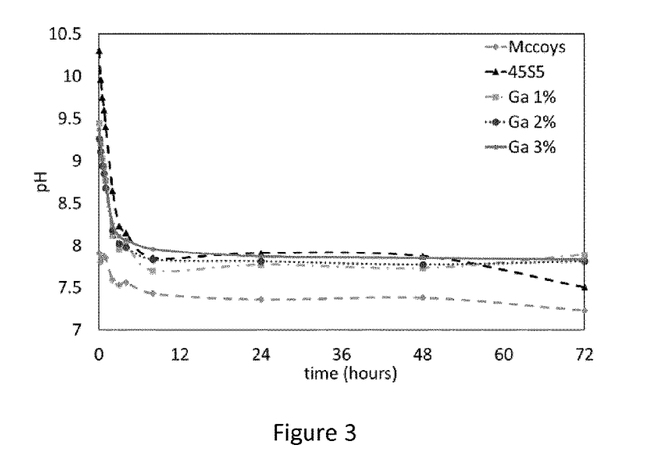
FIG. 3 shows pH of conditioned media containing Ga-doped bioactive glass compositions.

As shown in FIG. 3 the conditioned media shows a significant rise in pH as sodium and calcium ions rapidly leach from the glass in the surrounding media. pH readings taken directly after conditioning the media are designated as time point 0 in FIG. 3. Deviations from neutral pH are known to have detrimental effects on cell viability/proliferation, furthermore it is known that the body naturally buffers pH.

Therefore the conditioned media was incubated at 37° C. in a humidified atmosphere of 5% $CO_2$ for up to 72 hours to buffer the pH. McCoy's media was used as a control and it is clearly evident over the course of 72 hours the pH of the media fluctuated marginally from 7.91 at time point 0 to 7.23 at 72 hours, both readings within the physiological pH range acceptable for cell growth and maintenance.

In contrast 10 mg/ml of 45S5 control glass significantly elevated the pH of the media and at time point 0 a reading of 10.3 was recorded and a gradual decline was observed over the course of 72 hours (1 hour, 9.4, 2 hours, 8.65, 8 hours 7.85). Conditioned media generated by the addition of 10 mg/ml of Ga 1% (Example 1), Ga 2% (Example 2) and Ga 3% (Example 3) gallium doped bioactive glass also exhibited a similar trend, as a high pH was recorded for each glass composition at time point 0 (Ga 1%, pH 9.45, Ga 2% pH 9.26 and Ga 3% pH 9.37). At 24 hours the pH of all gallium containing conditioned media had decreased to physiologically acceptable levels where cell growth is viable (Ga 1%, pH 7.77, Ga 2% pH 7.81 and Ga 3% pH 7.87). Beyond 24 hours negligible changes in pH were observed. Therefore in following experiments the media was conditioned for 24 hours and then placed in the incubator for 24 hours to neutralise before being used. Neutralising the pH in this way eliminated any potential cytotoxic effects of the glass conditioned media due to lethal pH.

Cell cytotoxicity was analysed using MTT viability assay (Thermo Fisher), where 5000 cells per well of both Saos-2 and NHOst cells were cultured using conditioned media containing 10 mg/ml respective glass compositions (Examples 1-3), for a period of 72 hours. 10 μM Etoposide was used as a positive control, while cells grown using normal cell media served as a negative control. For the MTT assay, a 12 mM stock solution of 3-(4,5-dimethylthiazol-2-yl)-2,5-diphenyltetrazolium bromide (MTT) was prepared as per manufacturer's instructions and diluted 1/10 in phenol red free media before being added to the cells, which were incubated for 4 hours at 37° C. Following the incubation 75 μl of treatment was removed and 50 μl of Dimethyl sulfoxide (DMSO) was added and left to incubate at 37° C. for 10 minutes. Metabolically active cells reduce MTT to formazan and after formazan extraction the optical density was measured using a spectrophotometer (at 570 nm). This assay was performed in quintuplicate.

Figure 6:
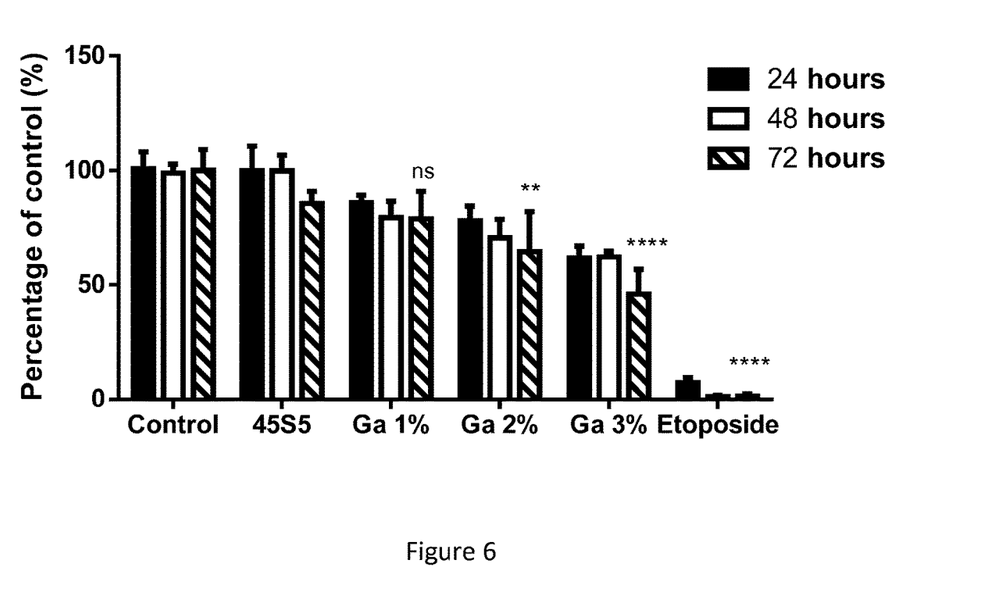
FIG. 6 shows Saos-2 cell viability following treatment with pH neutralised conditioned media containing Ga-doped bioactive glass compositions over 72 hours.
Figure 7:
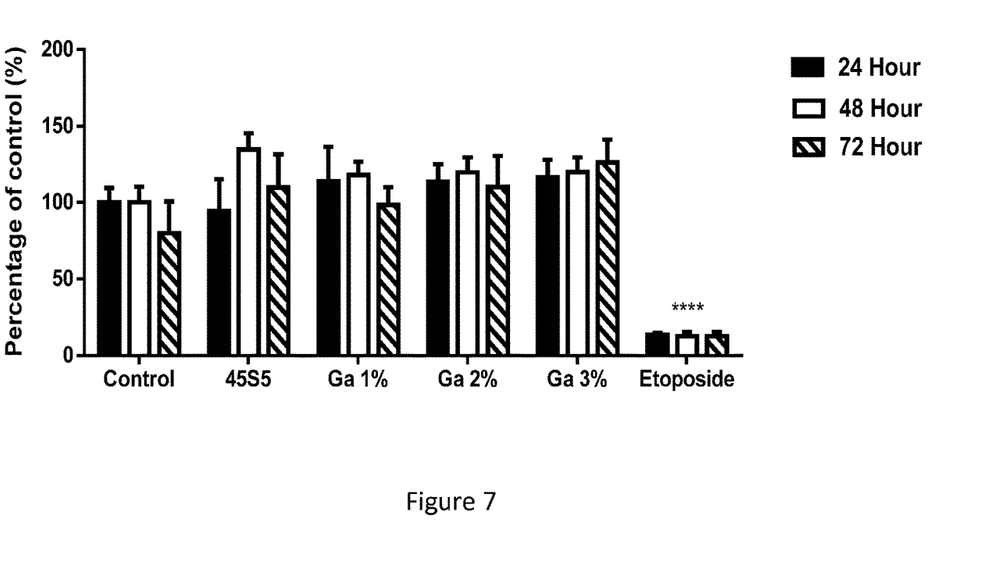
FIG. 7 shows NHOst cell viability following treatment with pH neutralised conditioned media containing Ga-doped bioactive glass compositions over 72 hours

No significant reduction in Saos-2 cell viability was observed between the positive control (unconditioned media) and the gallium free control glass (45S5). However a steady but significant decrease in Saos-2 cell viability was observed with increasing gallium oxide content in a dose response manner (Ga 2% (Ex2) $p<0.01$ and Ga 3% (Ex3) $p<0.0001$) as shown in FIG. 6. After 72 hours in conditioned Ga 3% (Ex3) conditioned media Saos-2 cell viability was less than 50%. In contrast conditioned media from the glasses showed no cytotoxic effects against normal human osteoblast cells as shown in FIG. 7. In each experiment 10 nm etoposide was used as a positive control and a known inducer of cell death ($p<0.0001$).

Cell Viability Assay 10,000 cells per well were seeded of both Saos-2 and NHOst cells and treated for 72 hours with conditioned media containing the dissolution products of 45S5, Ga 1% (Ex 1), Ga 2% (Ex 2) and Ga 3% (Ex 3) at a concentration of 10 mg/ml. Following the incubation period, a positive control of dead cells was established by incubating cells with 70% ethanol for 30 minutes. Cells treated with regular growth media served as a negative control. The polyanionic dye calcein-green is well retained within live cells, producing an intense uniform green fluorescence. Ethidium homodimer-1 (EthD-1) enters cells with damaged membranes and undergoes a 40-fold enhancement of fluorescence upon binding to nucleic acids, thereby producing a bright red fluorescence in dead cells. To stain Saos-2 cells working concentrations of calcein-green at 0.5 μM and EthD-1 at 2.5 μM were combined into one solution and used to treat cells, and to treat NHOst cells both calcein-green and EthD-1 were both prepared at a concentration of 0.5 μM. Cells were overlaid with 100 μl of staining solution and left to incubate for 45 minutes at room temperature. Cells were photographed using a fluorescent microscope at 100× magnification.

Figure 5:
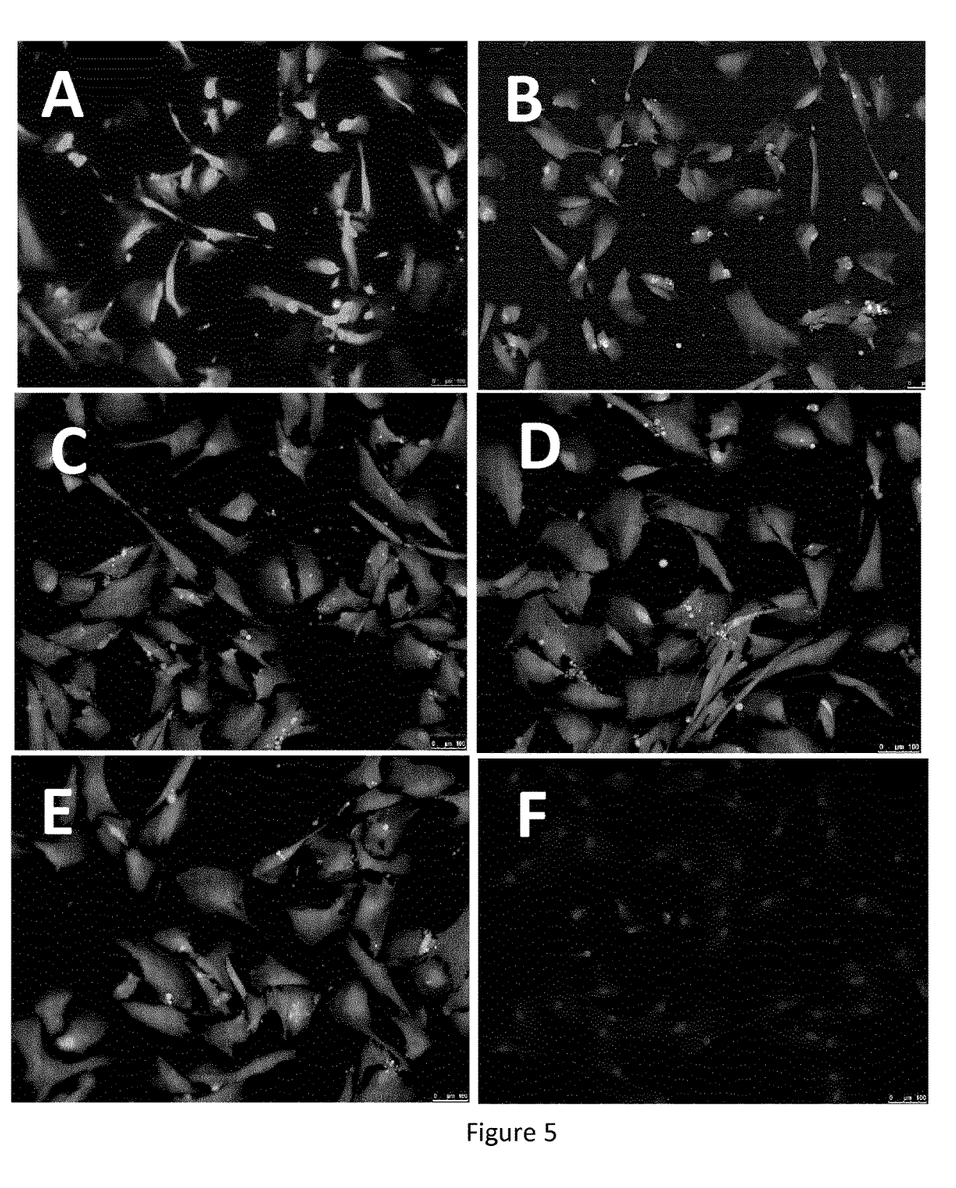
FIGS. 5A-5F shows fluorescence images of live/dead staining of NHOst-osteoblasts cultured for 72 hours in conditioned media containing Ga-doped bioactive glass compositions.

It was found that media containing Ga 3% glass significantly increases osteosarcoma (tumorous) cell death relative to the Ga 1% and Ga 2% glasses and 45S5 control as shown in FIG. 4 where FIG. 4A shows cells after treatment with McCoy basal media, FIG. 4B shows cells after treatment with conditioned media containing 45S5 Bioglass™ (control), FIG. 4C shows cells after treatment with conditioned media containing Ga 1% (Ex 1) bioactive glass composition, FIG. 4D shows cells after treatment with conditioned media containing Ga 2% (Ex 2) bioactive glass composition, FIG. 4E shows cells after treatment with conditioned media containing Ga 3% (Ex 3) bioactive glass composition and FIG. 4F shows cells after a 1 nM Etoposide treatment as a positive inducer of cell death. A significant increase in dead cells was observed between the 45S5 control glass and the Ga 1% and Ga 2% glasses whilst with the Ga 3% glass all cells appeared dead. In contrast, the Ga 3% glass remained non-toxic to osteoblast (non-tumorous) cells (see FIG. 5 where FIG. 5A shows cells after treatment with McCoy basal media, FIG. 5B shows cells after treatment with conditioned media containing 45S5 Bioglass™ (control), FIG. 5C shows cells after treatment with conditioned media containing Ga 1% (Ex 1) bioactive glass composition, FIG. 5D shows cells after treatment with conditioned media containing Ga 2% (Ex 2) bioactive glass composition, FIG. 5E shows cells after treatment with conditioned media containing Ga 3% (Ex 3) bioactive glass composition and FIG. 5F shows cells after a 1 nM Etoposide treatment as a positive inducer of cell death).

Experiments described above were performed with at least three independent samples per data point. Data were analysed using SPSS version 21 and GraphPad Prism 6. MTT, ICP and pH results are expressed as the mean±standard deviation. To compare cell viability between different time points and glass compositions Two-way ANOVA and Tukey's multiple comparisons test was conducted to test for significance with statistically significant values defined as $P<0.05$. Fluorescent microscopy and Live/Dead staining was used to distinguish between viable and non-viable cells results are qualitative and clearly indicate cell cytotoxicity or lack of.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A bioactive glass composition comprising:
   4 to 10 mol % gallium oxide ($Ga_2O_3$);
   25 to 75 mol % silicon dioxide;
   10 to 30 mol % calcium oxide and/or strontium oxide;
   1 to 30 mol % sodium oxide; and
   1 to 15 mol % phosphorous pentoxide.

2. A bioactive glass composition according to claim 1 comprising between 39.0 and 40.0 mol% silicon dioxide.

3. A bioactive glass composition according to claim 1 further comprising one or more of the following components:
   $K_2O$: from 0 to 15 mol %
   MgO: from 0 to 15 mol %
   ZnO: from 0 to 10 mol %
   $CaF_2$: from 0 to 15 mol %
   $CaCl_2$: from 0 to 15 mol %
   $B_2O_3$: from 0 to 10 mol %
   $Ag_2O$: from 0 to 10 mol %.

4. A bioactive glass composition according to claim 1 comprising from 35 to 55 mol % silicon dioxide.

5. A bioactive glass composition according to claim 1 comprising from 35.5 to 45 mol % silicon dioxide.

6. A bioactive glass composition according to claim 1 comprising from 27.0 to 30.0 mol % calcium oxide.

7. A bioactive glass composition according to claim 1 comprising from 24.5 to 27.0 mol % sodium oxide.

8. A bioactive glass composition according to claim 1 comprising from 2.7 to 3.0 mol % phosphorous pentoxide.

9. A method of treating bone cancer using a bioactive glass composition according to claim 1.

10. A bioactive glass composition comprising $(Ga_2O_3)_x(SiO_2)_{46.1-3x}(CaO)_{26.9}(Na_2O)_{24.4}(P_2O_5)_{2.6}$ wherein x satisfies $1 \leq x \leq 10$.

11. A bioactive glass composition according to claim 10, wherein x satisfies $4 \leq x \leq 10$.

* * * * *